United States Patent
Aoki et al.

[11] Patent Number: 6,112,593
[45] Date of Patent: *Sep. 5, 2000

[54] PORTABLE NON-DESTRUCTIVE INSPECTION DEVICE AND SUPPORT CASING THEREFOR

[75] Inventors: Shigenori Aoki, Ibaraki-ken; Tohru Miyata, Tsuchiura; Seigo Kikuchi, Matudo; Shigeru Miwa, Ibaraki-ken; Hajime Mizunoya, Tsuchiura; Takenori Hiroki, Ibaraki-ken, all of Japan

[73] Assignee: Hitachi Construction Machinery Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/188,372

[22] Filed: Nov. 10, 1998

[30] Foreign Application Priority Data

Nov. 14, 1997  [JP]  Japan .................................. 9-331135

[51] Int. Cl.⁷ .................................................. G01H 17/00
[52] U.S. Cl. ........................................................... 73/431
[58] Field of Search ............................. 73/431, 596, 598, 73/600; 374/208; 248/904; 206/305

[56] References Cited

U.S. PATENT DOCUMENTS

| | | |
|---|---|---|
| 2,338,695 | 1/1944 | Lingel . |
| 2,855,257 | 10/1958 | Barker et al. ............................. 73/431 |
| 2,966,257 | 12/1960 | Littlehohn ................................ 73/431 |
| 3,412,614 | 11/1968 | Mazurkevics ............................ 73/431 |
| 4,424,899 | 1/1984 | Rosenburg . |
| 4,578,586 | 3/1986 | Preston .................................... 73/431 |
| 5,640,155 | 6/1997 | Srpinger ................................... 73/431 |

FOREIGN PATENT DOCUMENTS

| | | | |
|---|---|---|---|
| 0228345 | 10/1986 | Japan ...................................... 73/598 |
| 822898 | 11/1959 | United Kingdom .................... 73/598 |

*Primary Examiner*—Robert Raevis
*Attorney, Agent, or Firm*—Mattingly, Stanger & Malur

[57] ABSTRACT

A non-destructive inspection device has an inspection unit body and a support casing which is used as a set-up type device by combining the inspection unit body and the support casing in ordinary inspection, and is used as a portable type device by separating them for special inspection situations involving narrow places or high places. The support casing can be freely combined to or separated from the inspection unit body. When combining the two components, the non-destructive inspection device can carry out the inspection based on a stable set-up mode in the same way as conventional devices. When separated, the inspection unit body is used as a portable device.

6 Claims, 8 Drawing Sheets

PORTABLE NON-DESTRUCTIVE INSPECTION DEVICE AND SUPPORT CASING THEREFOR

BACKGROUND OF THE INVENTION

1. Field of the Invention

The present invention relates to a portable non-destructive inspection device and a support casing therefor, and more particularly, to a structure suitable for a portable ultrasonic detector.

2. Description of the Related Art

As one example of the non-destructive inspection device an ultrasonic detector has been well known. This ultrasonic detector is used for inspecting defects in the inside of a sample to be inspected. In the ultrasonic detector, a probe emits ultrasonic waves toward the sample through a vehicle of ultrasonic waves and receives echo waves returned from the sample due to reflection on the sample. Conventional ultrasonic detectors are usually divided into two types, that is, a set-up type and a portable type which are respectively dependent on situations of use. The ultrasonic detector of the set-up type is ordinarily a large-sized device and therefore the device body thereof is set up at a specific place. When carrying out the inspection by using the ultrasonic detector of the set-up type, the sample to be inspected is mounted on the device body of the ultrasonic detector. On the other hand, the ultrasonic detector of the portable type is used to carry out the inspection on the condition that an inspector takes it to the place where the sample is placed. Namely, when using the ultrasonic detector of the portable type, the inspector carries it to the place where the object to be inspected, or the large-sized sample such as a building and so on exists, and carries out the inspection for the object there.

The conventional ultrasonic detectors were respectively produced as either one of the set-up type or the portable type and there was not any device capable of being used as both of the two types. However, users of ultrasonic detectors have sought a device which can be used selectively as the set-up type or the portable type depending upon the object to be inspected. This configuration has been requested not only for the ultrasonic detector but also for non-destructive inspection devices generally.

SUMMARY OF THE INVENTION

It is an object of the present invention is to provide a portable non-destructive inspection device, such as a portable ultrasonic detector, capable of being used as a set-up type or a portable type in accordance with selection of an inspector, and therefore serving as both the set-up type device and the portable type device all in one.

It is another object of the present invention is to provide a support casing suitable for the portable non-destructive inspection device which can be used as the set-up type or the portable type in accordance with arbitrary selection.

A non-destructive inspection device of the present invention is comprised of an inspection unit body and a support casing which can be combined into one or separated. The non-destructive inspection device is used as the set-up type by combining the inspection unit body and the support casing when carrying out the ordinary inspection, and is used as the portable type by separating the inspection unit body from the support casing when carrying out the special inspection in narrow places or high places and the like. Thus, the combination for the device of the set-up type and the separation for the device of the portable type cause the non-destructive inspection device to have two functions of the set-up type and the portable type all in one. The support casing can be freely combined to or separated from the inspection unit body. When combining the inspection unit body and the support casing, the non-destructive inspection device carries out measurement and inspection based on a stable set-up state in the same way as the conventional devices.

In the non-destructive inspection device, the inspection unit body has an input and output section, a signal processing section, a display section and an operating section. Also, the support casing has a section through which the inspection unit body is fit into and a section for stabilizing a center of balance. The inspection unit body is capable of carrying out the measurement and inspection and has all components necessary for the measurement and inspection. On the other hand, when using the non-destructive inspection device as the set-up type, the support casing must be combined with the inspection unit body. For that, it is indispensable for the support casing to have the section in which the inspection unit body fits. Further, it is preferable for the support casing to have the section for stabilizing the center of balance in order to put the inspection unit body down stably when the above-mentioned non-destructive inspection device is used as the set-up type.

It is especially preferable that the above-mentioned inspection unit body is an ultrasonic detector.

In the non-destructive inspection device, it is preferable for the support casing to have a power source. This power source is a comparatively large-sized one having a high electric power supply performance, because it may be arranged in the side of the support casing.

In the non-destructive inspection device, further, a power source line connection terminal for connecting the power source in the support casing and an electric circuit section within the inspection unit body is arranged. The power source arranged in the support casing is used for operating the built-in electric circuit section such as a signal processing section and the like in the inspection unit body on the occasion of selecting the use of the set-up type. In this case, therefore, the connection terminal for connecting the electric circuit section of the inspection unit body and the power source is disposed at a boundary part between them. The connection terminal is usually disposed at the above-mentioned section in which the inspection unit body fits into the support casing.

In the non-destructive inspection device, the above-mentioned power source is preferably used as the section for stabilizing the center of balance. Since the power source arranged in the support casing may be a large-sized and heavy one, the power source can be used as the above-mentioned section for stabilizing the center of balance.

In the non-destructive inspection device, an exclusive power source can be arranged only for the inspection unit body which is used separately. When causing the inspection unit body to be separated from the support casing and using it as the device of the portable type independently, it is necessary for the inspection unit body to be provided with the exclusive power source from the point of view of the configuration.

In the non-destructive inspection device, the exclusive power source is an external power source. The exclusive power source is preferably added to the inspection unit body as an external component.

In the non-destructive inspection device, the inspection unit body may have a built-in battery. The exclusive power source may be built in the inspection unit as the built-in battery. On this occasion, in addition to a case of the separation, even if the inspection unit body and the support casing are combined, the exclusive battery may be used as the power source.

In the non-destructive inspection device, the support casing has an interface used for connecting internal equipments and external equipments through signal lines. The use of the set-up type is general for the non-destructive inspection unit, when carrying out a usual inspection in the state of being connected to the other external equipments, such as a personal computer and the like, which execute data processing and data management by using the measured data transmitted from the non-destructive inspection unit. Then, for the purpose of connection between the inspection unit body and the external equipment, it is preferable to arrange the interface including a signal distributing section and various connection terminals in the side of the support casing. The signal processing section and the like arranged within the inspection unit body transmits the data stored therein to the external equipments through the interface arranged in the support casing.

In the non-destructive inspection device, a signal line connection terminal is arranged between the inspection unit body and the support casing. In case of employing the configuration of transmitting data from the signal processing section and the like arranged within the inspection unit body to the external equipments through the interference, the signal line connection terminal is disposed at the boundary part of the inspection unit body and the support casing.

In the non-destructive inspection device, a connection terminal common to both a power source line and a signal line is arranged between the inspection unit body and the support casing. When forming connection terminals respectively used for the power source line and the signal line as the common terminal, handling as to the combination and separation of the inspection unit body and the support casing is simplified and improved. In this case, the power source line and the signal line in the side of the inspection unit body are bundled up to make one common electric cable.

In the portable non-destructive inspection device, the section of the support casing that receives the inspection unit body a hollow space having an opening and the inspection unit body is fitted into the hollow space through the opening.

In accordance with the non-destructive inspection device of the present invention, such as the ultrasonic detector and the like, the inspection unit body is originally made to be used as the portable type and the support casing capable of being freely put on and taken off is added to the inspection unit body, the inspection device is usually used as the set-up type device by combining the inspection unit body and the support casing, while the inspection device is used as the portable type device for the measurement and inspection at the specific places by separating the inspection unit body from the support casing. Consequently, the non-destructive inspection device of the present invention is very useful and valuable as the products, and further satisfies the requests on the spot where the measurement and inspection is carried out. Further, this non-destructive inspection device serves as both the set-up type device and the portable type device all in one. Thereby, the cost required for preparing the non-destructive inspection device can be decreased and the convenience of using the non-destructive inspection device is very improved.

The inspection unit body is made to become light in order to use it as the portable type, and when using it as the set-up type by combining it with the support casing, the weight (the section for stabilizing the center of balance) arranged in the support casing improves stability of the set-up type device. Also, in the structure of arranging the power source in the support casing, the power source can be used as the above-mentioned weight and therefore the whole configuration of the non-destructive inspection device can be simplified.

In the structure capable of combining the inspection unit body and the support casing therefor or separating them, since the common electric cable and the common connection terminal are used as to the configuration of the power source line and the signal line, the combination and separation can be performed easily from the point of view of the electric circuit section.

Since the above-mentioned combination and separation is performed by fitting the inspection unit body into the opened hollow space formed in the front part of the support casing or removing the former from the latter, the handling thereof is very easy.

DESCRIPTION OF THE PREFERRED EMBODIMENTS

Hereinafter, preferred embodiments of the present invention will be described with reference to the accompanying drawings.

Figures 1A, 1B, 1C:
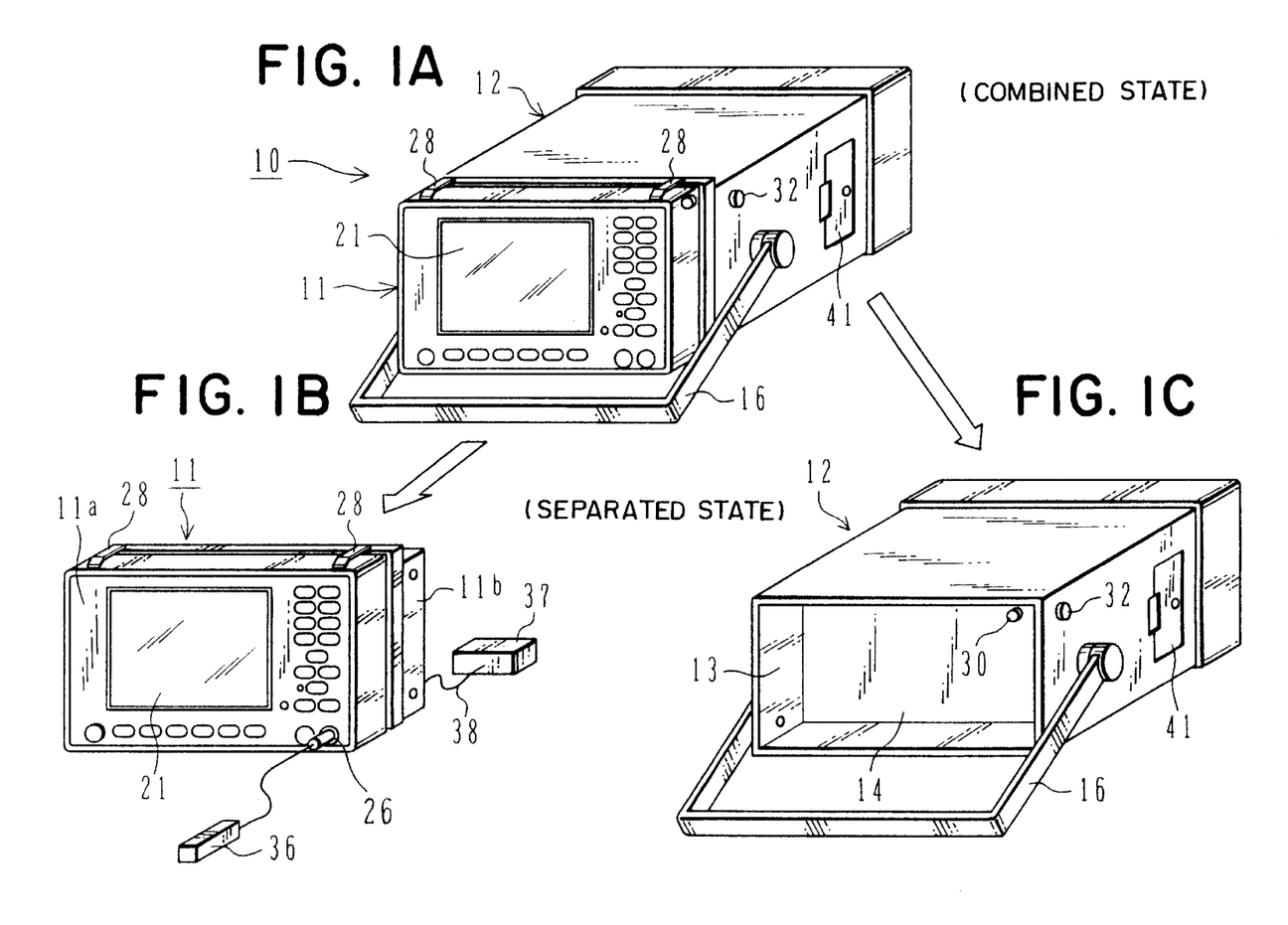
FIGS. 1A–1C show perspective views of a portable ultrasonic detector of a typical embodiment according to the present invention, which include FIG. 1A concerning a combination of an ultrasonic detecting section and a casing section, and FIGS. 1B and 1C respectively concerning the ultrasonic detecting section and the casing section, which are separated.

FIGS. 1A–1C show a portable ultrasonic detector as a typical embodiment of the portable non-destructive inspection device of the present invention. This portable ultrasonic detector 10 comprises a device body for carrying out an inspection by making use of ultrasonic waves, a support casing 12 for supporting the device body 11, which is combined with the device body when using the device body 11 as a set-up type. Although the ultrasonic detector 10 is originally manufactured as a portable product, it is further manufactured to be usable as the set-up type in response to the situations of use by combining the support casing 12 to be freely put on or taken off of the device body 11. From this point of view, the device of this embodiment is called a "portable ultrasonic detector". In this embodiment, the portable ultrasonic detector will be explained. However, the portable non-destructive inspection device of the present invention is not limited to this embodiment. The characteristic configuration of the present invention can be applied to other inspection devices which operate by means of different measuring methods.

FIGS. 1A–1C include a perspective view (1A) showing the state of combining the device body 11 and the support casing 12, and perspective views (1B, 1C) respectively showing the device body 11 and the support casing 12 which are separated in order to clarify the feature of the configuration of the portable ultrasonic detector 10. FIG. 1A shows the state of the device body 11 used as the set-up type and FIG. 1B shows the state used as the portable type. In case of the use as the set-up type, the ultrasonic detector 10 is usually placed on a desk, for example. Also, in case of the use as the portable type, in a practical manner, the device body 11 is carried by an inspector with a shoulder belt to a spot (a narrow spot or a high spot and the like) where an object to be inspected exists. In FIGS. 1A–1C, in order to clarify that the portable ultrasonic detector 10 has the structure capable of separating itself into the device body 11 and the support casing 12, a schematic illustration of the structure is shown.

The support casing 12 is made of metal plates, for example, so as to have a box shape, and has strength necessary for supporting the device body 11. The support casing 12 has an opening 13 at its front part as shown in FIG. 1C. The opening 13 is used as a part in which the device body 11 is fit into the support casing and therefore is formed as a hollow space. The structure comprised of the opening 13 or the hollow space has a function as an attached section by which the support casing 12 is attached to the device body 11. The opening 13 (the hollow space) has a bottom wall 14 and further the support casing 12 has an inner space in the inner part of the bottom wall 14 which corresponds to a partition or boundary. In the inner space of the support casing 12, a power source 15 (shown by dotted lines in FIGS. 6 and 7) is arranged at the place close to the bottom of the support casing 12. The power source 15 is a means of supplying electric power to an electric circuit section included in the device body 11 when using the portable ultrasonic detector 10 as the set-up type by combining the device body 11 and the support casing 12. Also, the power source 15 has sufficient weight and therefore, on the occasion of combining the device body 11 and the support casing 12 to make the set-up type device, the power source 15 serves as a weight for stabilizing the set-up state of the portable ultrasonic detector 10 when setting the support casing 12 in raised or tilted positions. Namely, the power source 15 is used as a weight for stabilizing a center of balance. In addition, except for the power source, other different things may be used as the weight. A handle 16 which is rotatably installed at the place close to the opening 13 is arranged between the both side walls of the support casing 12. This handle 16 serves as a support, when combining the device body 11 and the support casing 12 and causing the support casing 12 to be arranged with a tilted posture.

Figure 2:
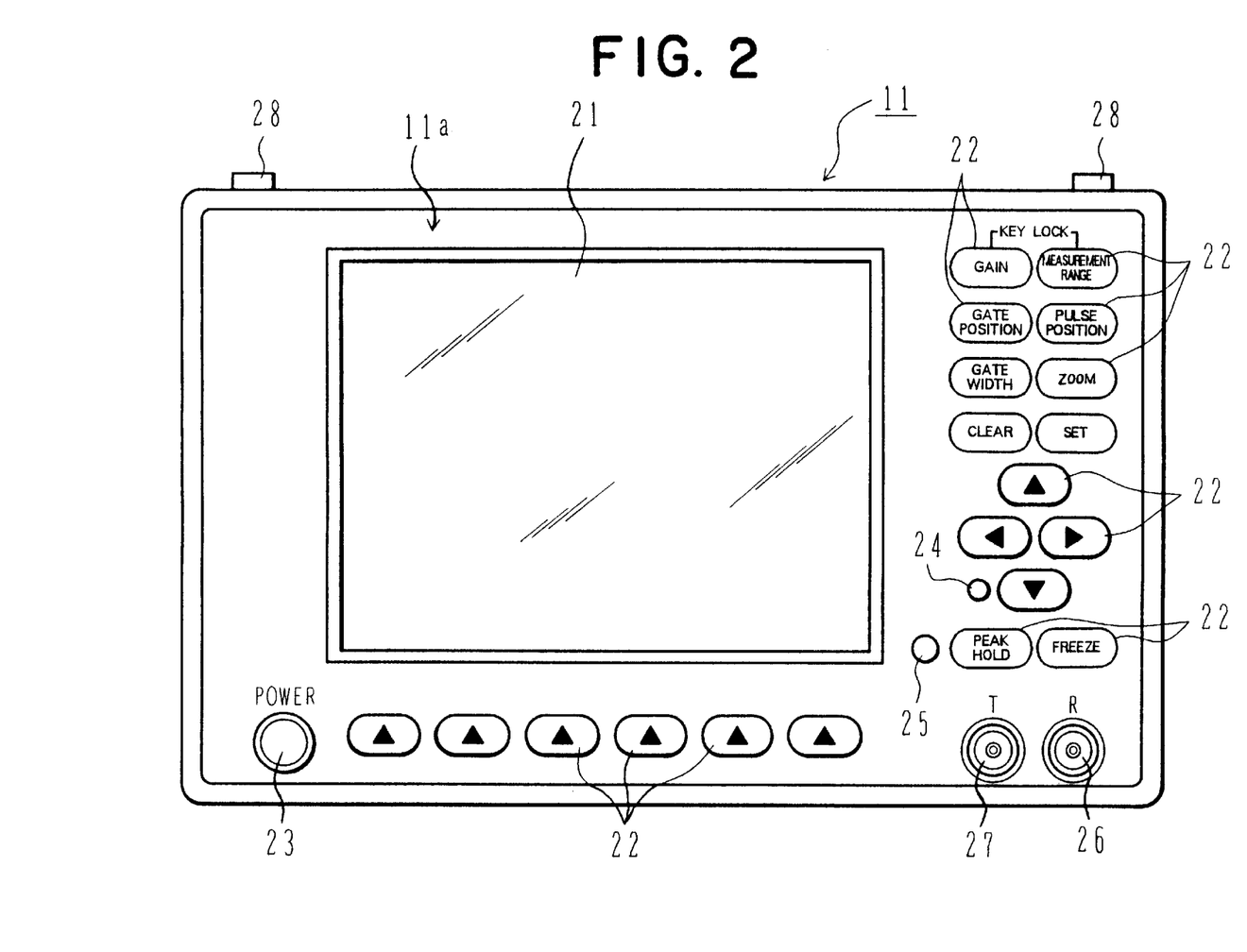
FIG. 2 is a front view of the ultrasonic detecting section.
Figure 3:
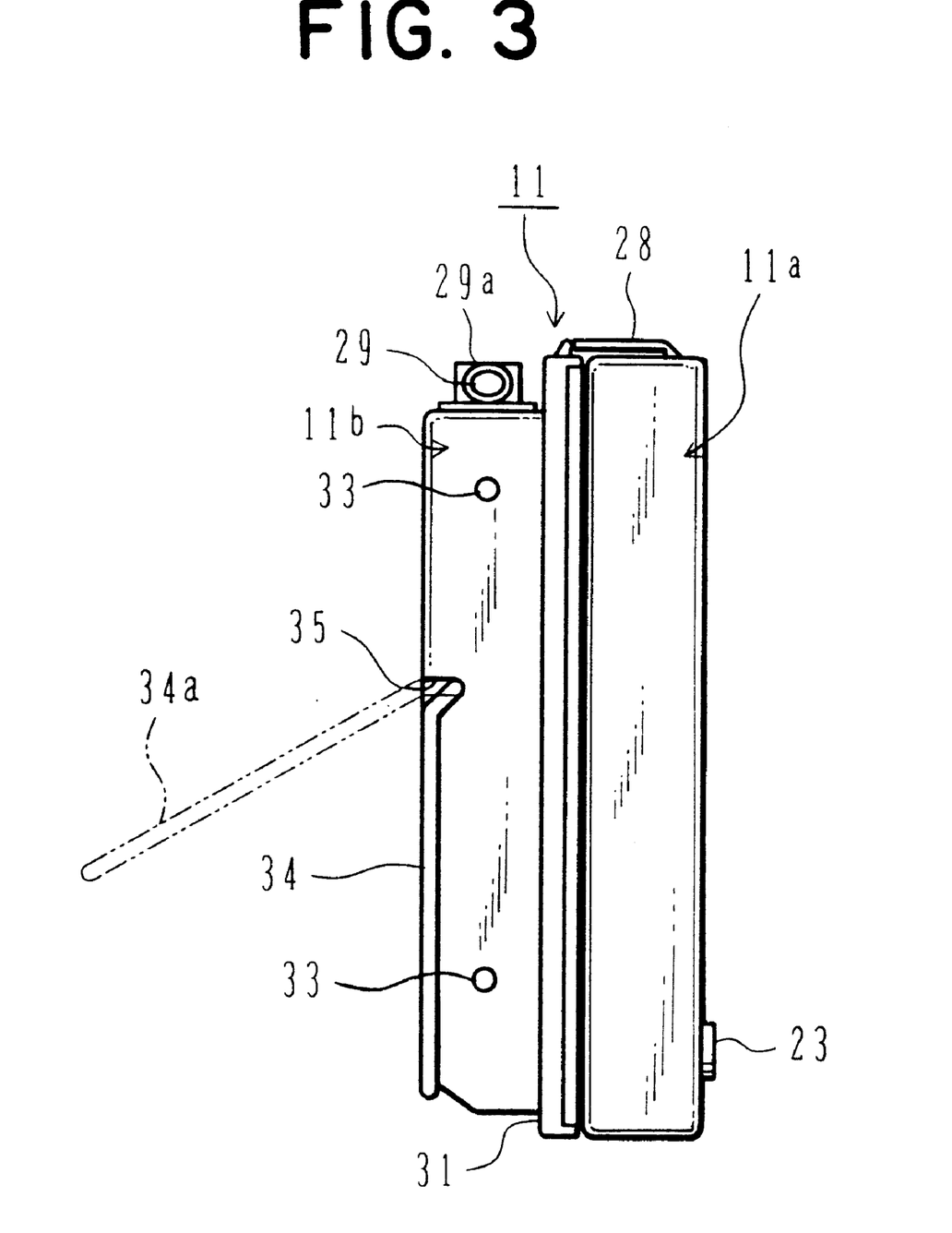
FIG. 3 is a side view of the ultrasonic detecting section.
Figure 4:
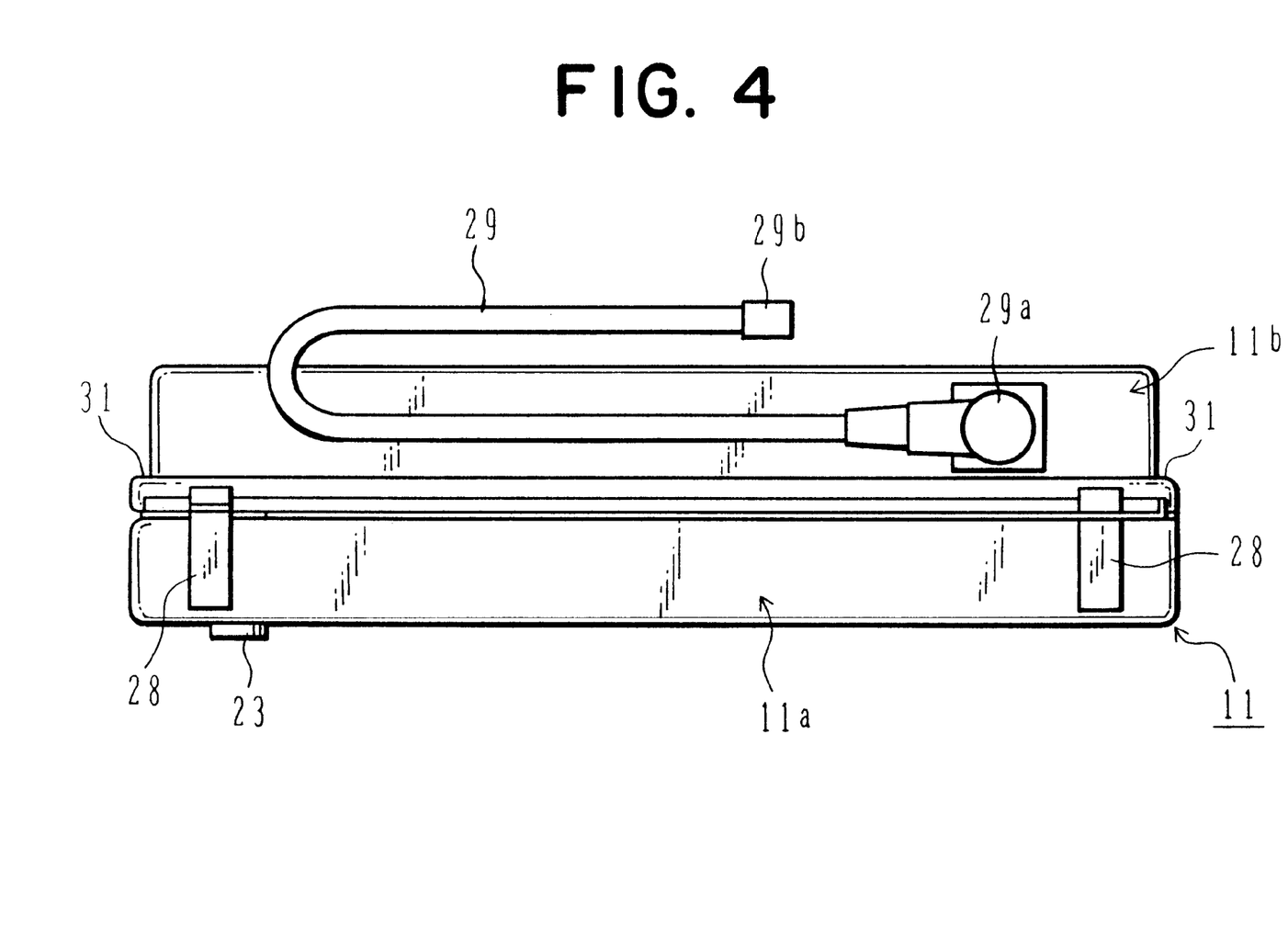
FIG. 4 is a plan view of the ultrasonic detecting section.

FIGS. 2–4 show an example of the device body 11 which is separated and used as an ultrasonic detecting section. A display section 21 made from a liquid crystal is arranged in the front section of the device body 11. TFT is used as the liquid crystal for the display section 21, for example, and further the TFT is preferably made to have a large-sized color screen which is long from side to side. The display section 21 displays echo waves and the like which are obtained on the basis of measurement. In the periphery region of the display section 21, a plurality of various operating keys 22 are arranged that are used on the occasion of taking measurements, such a power source switch 23, a buzzer 24, a LED 25, an input terminal 26, and an output terminal 27 and the like. Suspended sections 28 are used for supporting a carrying band for the device body 11 and are arranged at two spots on both sides of the upper section of the device body 11. A rear section 11b is formed in the back side of the device body 11. The rear section 11b has the electric circuit section built-in. One end 29a of an electric cable 29 including a power source line and signal lines is connected to the upper section of the rear section 11b. The power source line and the signal lines are bundled in the electric cable 29 and further the electric cable 29 is used as a common cable. Another end 29b of the electric cable 29 is of a free state when the device body 11 is separated to be single, and further is connected to a connector (or a connection terminal) 30 arranged at the inner part of the opening 13 in the support casing 12 when the device body 11 is combined with the support casing 12. The connector 30 is used as a common connector for the power source line and the signal lines. Since the single electric cable 29 and the connector 30 as the common connector are utilized, the portable ultrasonic detector 10 can be easily handled when combining the device body 11 with the support casing 12 and separating the device body 11 from the support casing 12.

A difference 31 in level is formed at a periphery outer part of the device body 11, which is positioned at the boundary between the rear section 11b and a front section 11a thereof. When installing the device body 11 into the support casing 12, only the rear section 11b of the device body 11 is inserted into the opening 13 and the entire edge of the opening 13 engages the periphery part of the rear of the front section 11a. The device body 11 is fitted into the support casing 12 and is fixed to the support casing 12 with screws 32 and the like. Two threaded holes 33 to be combined with the screw 32 are formed in both side-walls of the rear section 11b of the device body 11. A support frame 34 is installed at a back-side lower section of the rear section 11b. Both ends of the support frame 34 are rotatably joined to both side-parts of the rear section 11b. The support frame 34 is tilted as shown by a dotted line 34a when raising the device section 11 in the separated state. An edge section restricts the position of the support frame 34 to determine a rotatable angle thereof.

As to the electric circuit section built into the rear section 11b of the device body 11, a plurality of circuit components respectively realizing various functions are arranged on a main board. An example of the electric circuit section is shown in FIG. 8. Also, when using the portable ultrasonic detector 10 as the set-up type by fitting the device body 11 into the support casing 12, the end 29b of the electric cable 29 is connected to the connector 30 arranged in the support casing 12 as mentioned above. The support casing 12 has a sub-board 43 built-in (shown in FIG. 7). When using the portable ultrasonic detector 10 as the set-up type, the electric circuit section within the device body 11 receives the electric power supplied from the power source 15 arranged within the support casing 12 through the electric cable 29 and thereby is operative.

On the other hand, when causing the device body 11 corresponding to the ultrasonic detecting section to be separated from the support casing 12 and using it independently as the portable type, it is required to add an exclusive power source, for example, an exclusive battery 37 to the device body 11. The battery 37 may be arranged on the outside of the device body 11 to supply the electric power to the electric circuit section through a power source line 38 as shown in FIGS. 1B and 8, or it may be built into the device body 11. When outside, the battery 37 can be carried by the inspector with a carrying belt, for example.

When the device body 11 is used independently as the portable type, as shown in FIG. 1B, a probe 36 is connected to the input terminal 26 thereof together with the addition of the exclusive battery 37.

Figure 5:
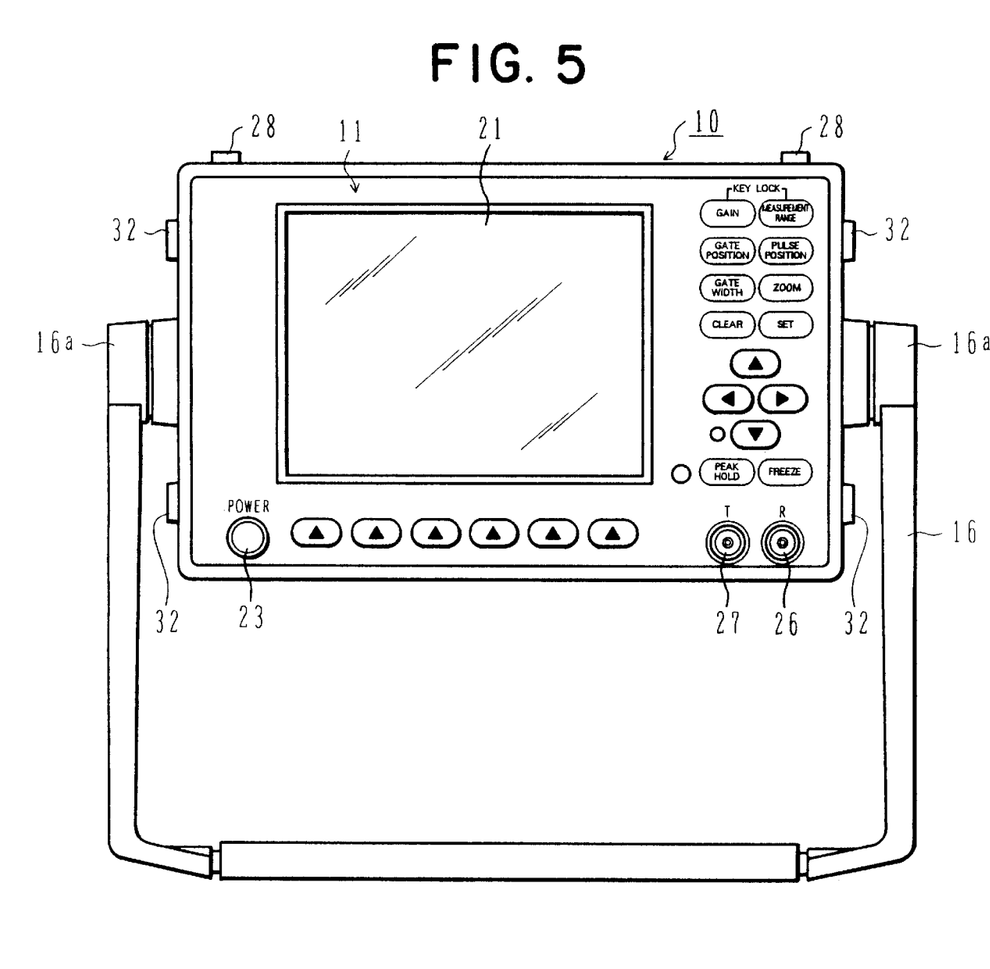
FIG. 5 is a front view of the ultrasonic detector formed by combining the ultrasonic detecting section and the casing section.
Figure 6:
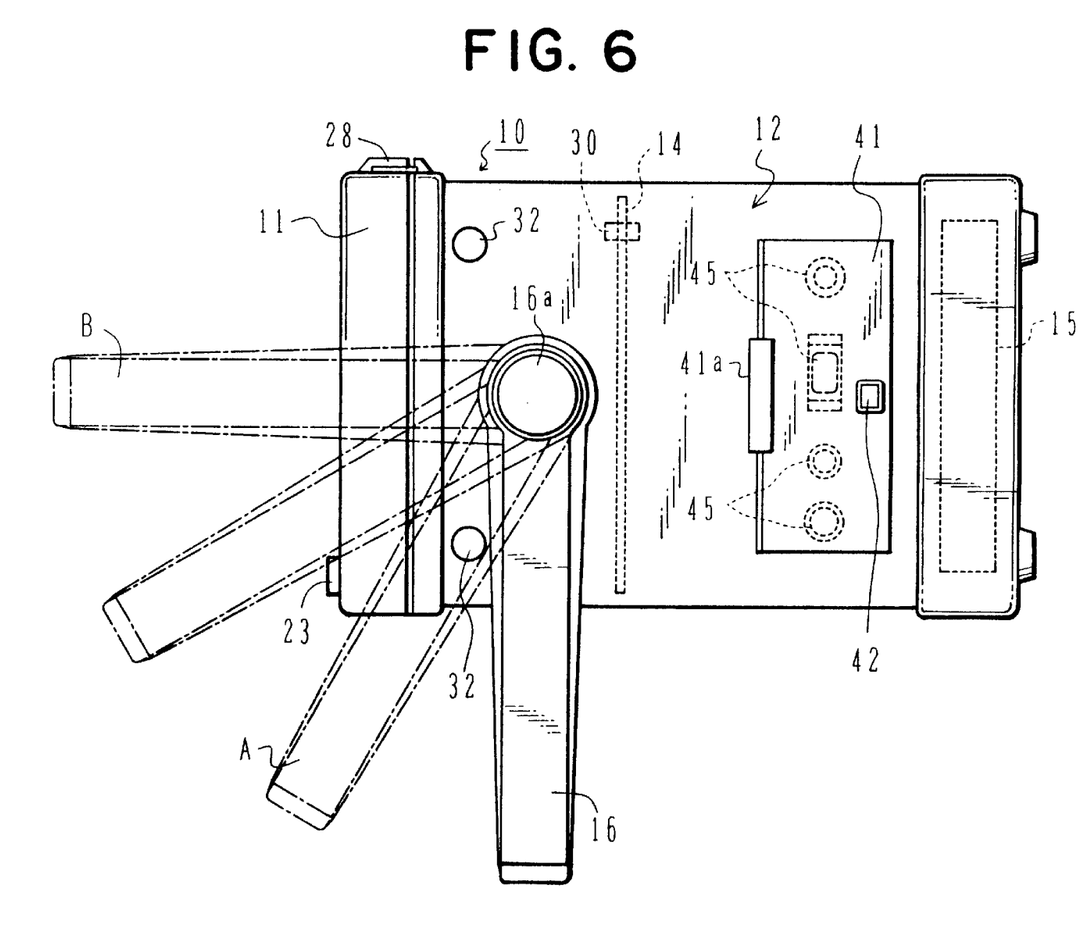
FIG. 6 is a side view of the ultrasonic detector.
Figure 7:
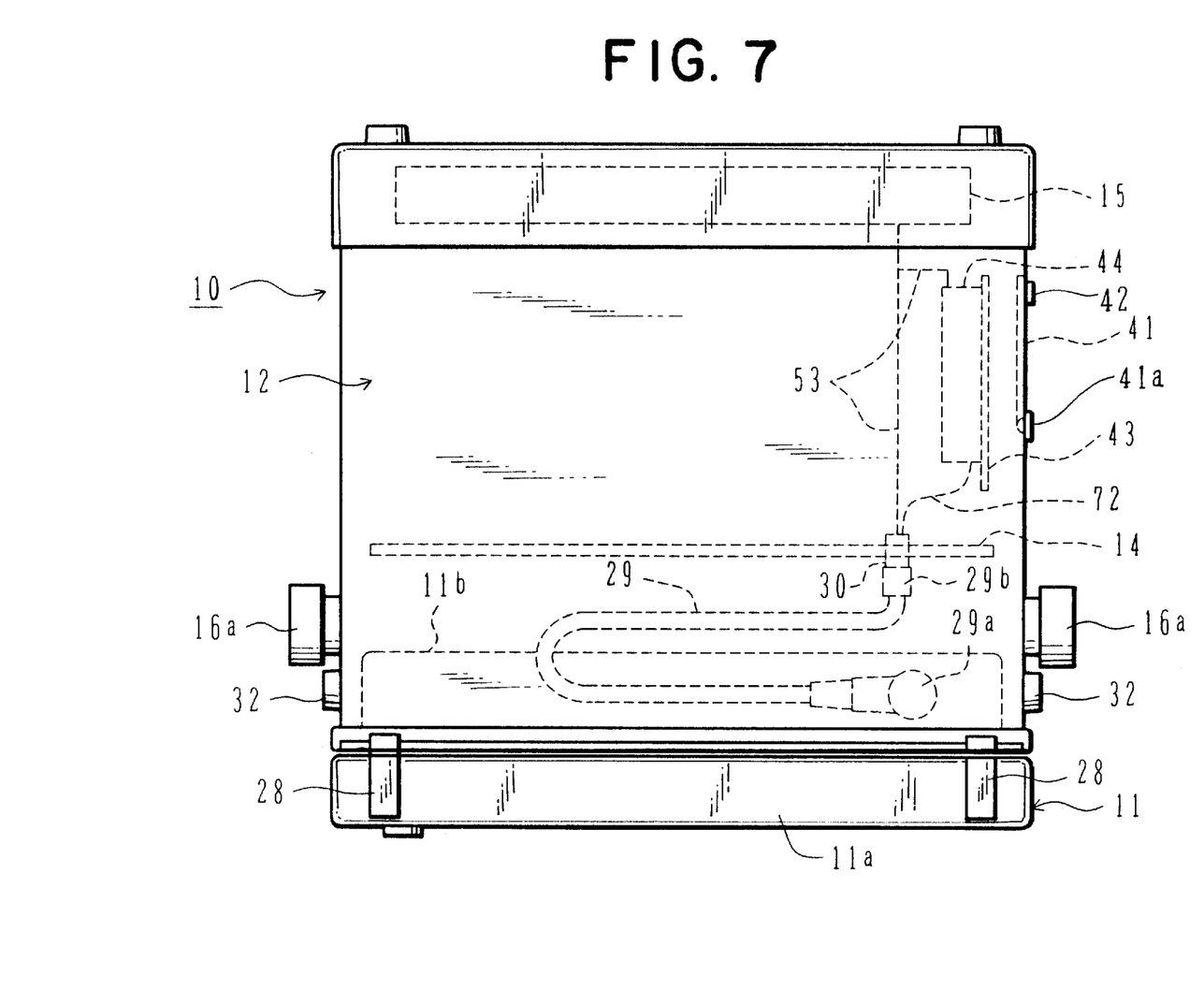
FIG. 7 is a plan view of the ultrasonic detector.
Figure 8:
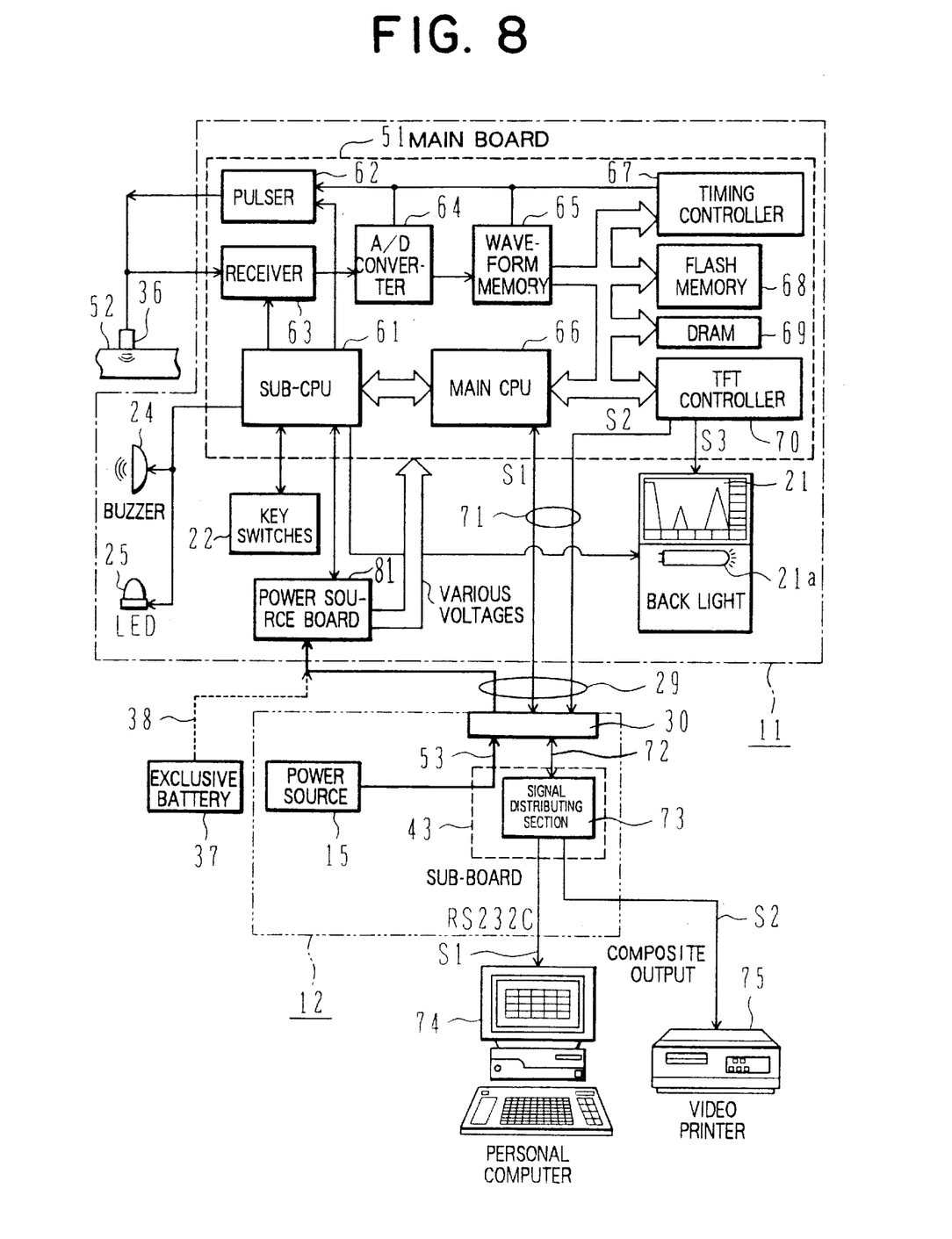
FIG. 8 is a block and connection diagram showing a system configuration of the ultrasonic detector.

FIGS. 5–7 show an example of the combination state of the device body 11 and the support casing 12. As mentioned above, the device body 11 is inserted into the opening 13 of the support casing 12 and fixed to it with the screws 32. On the occasion of the use as the set-up type, as shown in FIG. 6, the handle 16 is rotated around both connecting ends 16a to position A. When carrying the portable ultrasonic detector 10 of the combined manner, the handle 16 is used to obtain position B. The reference numeral 15 shown by a dotted line in FIGS. 6 and 7 denotes the above-mentioned power source arranged in the bottom of the support casing 12. Also, as shown in FIG. 6, a cover section 41 capable of being opened or closed is arranged in one-side wall of the support casing 12. The cover section 41 is rotated around a hinge 41a to open by operating a push button 42. The above-mentioned sub-board 43 is arranged in an area the support casing 12, which corresponds to the cover section 41. The sub-board 43 is provided with an interface 44 used for connecting the electric circuit section within the device body 11 and external equipments. This interface 44 includes a signal distributing section. When opening the cover section 41, a plurality of connectors 45 make their appearance, which are fixed to the sub-board 43 and to which the various external equipments can be respectively connected. Concretely, these connectors 45 are respectively connected with an external personal computer for processing data, a video printer, and a distance measurement device realizing a B-scope device, etc. The above-mentioned signal distributing section in the interface 44 has a function of distributing measurement signals sent from the electric circuit section within the device body 11 into connectors 45.

FIG. 8 is a block diagram showing the system configuration of the ultrasonic detector. In this system configuration, the device body 11 is combined with the support casing 12 an d the end 29b of the electric cable 29 is connected to the connector 30 being the common connector. Accordingly, the main board 51 in the device body 11 and the sub-board 43 in the support casing 12 are connected electrically. The above-mentioned power source 15 arranged within the support casing 12 supplies the electric power to the main board 51 through a power source line 53, the connector 30, and a power source line 54 included in the electric cable 29. The electric power supplied from the power source 15 is also given to the sub-board 43. When separating the device body 11 from the support casing 12, the power source 15 can not be used as the electric power supplier. In this case, the above-mentioned exclusive battery 37 shall be used.

The main board 51 is provided with the electric circuit section for carrying out the inspection and measurement as the ultrasonic detector. This electric circuit section includes a sub-CPU 61 controlling the operation of sending/receiving the ultrasonic waves. Signals used for the emission of the ultrasonic waves, which are outputted from the sub-CPU 61, are provided to a pulser 62 which outputs pulse signals to the probe 36. The probe 36 includes a piezoelectric element which transduces the pulse signals to the ultrasonic waves. The ultrasonic waves are emitted into the inside of a sample 52 to be inspected. If the sample 52 has defects in its inside, the defects generate defect echoes due to the reflection of the ultrasonic waves, which return to the probe 36. The defect echo ultrasonic wave is transduced to an electric echo signal by the piezoelectric element within the probe 36. This electric echo signal is sent to a receiver 63. The receiver 63, in which a gain parameter and the like is set by control signals given from the sub-CPU 61, receives the electric echo signal. The electric echo signal (waveform signal) which the receiver 63 receives as an analog signal is converted into a digital signal by an A/D converter 64 and afterward is stored in a waveform memory 65 in a digital mode. On the other hand, operating signals which are inputted through a plurality of key switches 22 (corresponding to the operating keys) are sent to the sub-CPU 61. The operations of the various key switches 22 is capable of providing the sub-CPU 61 with various instructions as to the measurement. As examples of the instructions based on the key switches 22, there are setting of gain, positions of pulses or gates, a width of gates, expansion of a waveform (zoom), peak holding, and a change of screen display contents in the display section 21 and the like, for example. Further, the sub-CPU 61 drives the buzzer 24 and a luminous indicating part (the LED 25 and the like) to provide messages to the inspector, if necessary.

The above-mentioned electric circuit section further includes a main CPU 66 for calculating and processing data obtained by the measurement. In relation to the main CPU 66, the electric circuit section includes a timing controller 67, a flash memory 68, a DRAM 69 and a TFT controller 70. The main CPU 66 produces image signals for making images and control signals which are obtained by processing the measured waveform data stored in the waveform memory 65, and sends these signals to the TFT controller 70. This TFT controller 70 controls image contents displayed on the display section 21 on the basis of the image signals and the control signals, that is, output signal S3 used for displaying the images. The display section 21 is the liquid crystal display section with a back light 21a. A drive signal of operating the back light 21a is provided from the sub-CPU 61. Also, the main CPU 66 outputs a signal S1 concerning the measurement data separately.

The signal S1 outputted from the main CPU 66 and a composite signal S2 outputted from the TFT controller 70 can be sent to the sub-board 43 through the signal lines 71 included in the electric cable 29, the connector 30 and the signal line 72. When the plural connectors 45 in the sub-board 43 are respectively connected to the personal computer 74 and the video printer 75, for example, the signals S1 and S2 are distributed to two routes by the signal distributing section 73 within the interface 44, and as a result the signal S1 is sent to the personal computer 74 and the signal S2 is sent to the video printer 75. In addition, the device body 11 includes a power source board 81 which can be connected with either one of the power source 15 and the exclusive battery 37.

In accordance with the above-mentioned embodiment, though the power source for causing the device body 11 to operate is disposed in the side of the support casing 12 on the occasion of combining the device body and the support casing, a power source of small size and high efficiency can be built into the device body 11 in advance. In this structure, in any case of the combination and the separation, the built-in power source can be always used. In the support casing 12, instead of the power source 15, other weights (various members for stabilizing a center of balance) may be arranged. Also, though the electric cable 29 was formed to be a common cable for both the power source line and the signal lines, and the connector 30 was formed to be a common connector, the present invention is not limited to these configurations. The power source line and the signal lines may be separated.

Although in the embodiment the support casing 12 was explained as a supporting instrument used only for an inspection unit body or the device body 11 of the ultrasonic detector 10, it can be recognized as an independent invention concerning a supporting instrument by itself, or a support casing capable of causing the conventional various portable inspection devices to operate in the set-up mode due.

What is claimed is:

1. A portable non-destructive inspection device comprising:

a portable ultrasonic detector having an input and output section, an external probe, a signal processing section, a display section having a display of a size sufficient to display echo waves and an operating section, and a support casing that supports said ultrasonic detector, wherein said ultrasonic detector can be freely combined to or separated from said support casing, and further, said portable non-destructive inspection device including:
   said support casing having an open hollow formed on a front section thereof that is used for receiving a part of said ultrasonic detector, and a section for stabilizing a center of balance at a bottom section thereof, and said support casing having side walls and a handle mounted on said side walls that rotates between a support position and a carrying position, wherein when said handle is in said support position, said front section of said support casing is supported by said handle, said part of said ultrasonic detector received in said open hollow is at a rear section of said ultrasonic detector, and when said ultrasonic detector is combined with said support casing by fitting said part into said open hollow so as to form a single combined device, the single combined device is used as a set-up type device in which an operating/displaying screen of said ultrasonic detector is placed at a front section of said single combined device, while when said ultrasonic detector is separated from said support casing, said ultrasonic detector is operable as a portable type devices, wherein said section for stabilizing a center of balance of said support casing has a power source having sufficient weight to stabilize the center of balance of the inspection device when said ultrasonic detector is combined with said support casing, and wherein said ultrasonic detector has an exclusive power source for use when said ultrasonic detector is separated from said support casing.

2. The portable non-destructive inspection device according to claim 1, further comprising a power source line connection terminal at said open hollow of said support casing, with which a power source line is connected, for connecting said power source within said support casing and an electric circuit section within said ultrasonic detector.

3. The portable non-destructive inspection device according to claim 2, wherein a signal line connection terminal with which signal lines are connected is arranged between said ultrasonic detector and said support casing.

4. The portable non-destructive inspection device according to claim 3, wherein a common connection terminal for both the power source line and the signal line is arranged between said ultrasonic detector and said support casing.

5. The portable non-destructive inspection device according to claim 1, wherein said exclusive power source is an external power source.

6. The portable non-destructive inspection device according to claim 1, wherein said support casing has an interface enabling connection with various external instruments by means of signal lines.

* * * * *